US011621087B2

(12) United States Patent  
Goudey et al.

(10) Patent No.: US 11,621,087 B2  
(45) Date of Patent: Apr. 4, 2023

(54) MACHINE LEARNING FOR AMYLOID AND TAU PATHOLOGY PREDICTION

(71) Applicant: International Business Machines Corporation, Armonk, NY (US)

(72) Inventors: Benjamin Goudey, Victoria (AU); Annalisa Jean Swan, Victoria (AU); Noel Garry Faux, Victoria (AU); Roslyn Hickson, Victoria (AU); Christine Schieber, Victoria (AU); Bowen Fung, Pasadena, CA (US)

(73) Assignee: International Business Machines Corporation, Armonk, NY (US)

(*) Notice: Subject to any disclaimer, the term of this patent is extended or adjusted under 35 U.S.C. 154(b) by 803 days.

(21) Appl. No.: 16/580,632

(22) Filed: Sep. 24, 2019

(65) Prior Publication Data

US 2021/0090746 A1 Mar. 25, 2021

(51) Int. Cl.
*G16H 50/70* (2018.01)
*G16H 50/30* (2018.01)
(Continued)

(52) U.S. Cl.
CPC ............ *G16H 50/70* (2018.01); *G06N 20/00* (2019.01); *G16H 50/00* (2018.01); *G16H 50/30* (2018.01); *G16H 70/60* (2018.01)

(58) Field of Classification Search
None
See application file for complete search history.

(56) References Cited

U.S. PATENT DOCUMENTS 7,794,948 B2    9/2010  Davies et al.
2002/0072859 A1* 6/2002  Kajimoto ............... A61B 5/162
                                                        600/300
(Continued)

FOREIGN PATENT DOCUMENTS

CN       106636398 A  *  5/2017  ........... C12Q 1/6883
JP       2005118026 A  *  5/2005
(Continued)

OTHER PUBLICATIONS

Bazenet et al., Plasma biomarkers for Alzheimer's disease: much needed but tough to find, Aug. 2012, Biomarkers in Medicine, vol. 6 (Year: 2012).*

(Continued)

*Primary Examiner* — Rachelle L Reichert
*Assistant Examiner* — Karen A Hranek
(74) *Attorney, Agent, or Firm* — Patterson + Sheridan, LLP

(57) ABSTRACT

Method and apparatus for predicting amyloid beta (Aβ) and phosphorylated tau (p-tau) biomarker levels in the cerebrospinal fluid (CSF) of patients. Embodiments include determining current values for a plurality of easily-measurable attributes of a first patient. Embodiments include analyzing data associated with a cohort of patients having known measurements of Aβ and p-tau biomarker levels, including determined values for the plurality of easily-measureable attributes. Embodiments include generating a predicted value for Aβ and/or p-tau biomarker levels for the first patient. Embodiments include generating a risk of the first patient developing AD at a future time, generating a probability of a patient's predicted rate of decline, and/or generating a probability of a patient's age at the onset of dementia, based on the predicted values for Aβ and/or p-tau biomarker levels.

20 Claims, 5 Drawing Sheets

(51) Int. Cl.
*G06N 20/00* (2019.01)
*G16H 70/60* (2018.01)
*G16H 50/00* (2018.01)
*G06K 9/62* (2022.01)
*G06N 5/00* (2006.01)

(56) References Cited

U.S. PATENT DOCUMENTS

| | | | | |
|---|---|---|---|---|
| 2010/0124756 | A1* | 5/2010 | Ray | G01N 33/6896 435/287.9 |
| 2011/0177509 | A1* | 7/2011 | Goate | C12Q 1/6883 536/24.31 |
| 2013/0116135 | A1 | 5/2013 | Doecke et al. | |
| 2014/0086836 | A1 | 3/2014 | Burnham et al. | |
| 2016/0139150 | A1* | 5/2016 | de Leon | G01N 33/6896 435/7.92 |
| 2017/0219611 | A1* | 8/2017 | Ward | G01N 33/6896 |
| 2019/0041404 | A1* | 2/2019 | Chirila | G16H 50/20 |
| 2019/0265256 | A1* | 8/2019 | Kiyohara | G01N 33/5091 |
| 2019/0272922 | A1* | 9/2019 | Albright | G06N 3/0445 |
| 2022/0157467 | A1* | 5/2022 | Katragadda | A61B 5/14546 |

FOREIGN PATENT DOCUMENTS

| | | | | |
|---|---|---|---|---|
| WO | WO-2007109749 A2 * | 9/2007 | | C07K 14/705 |
| WO | WO-2015020523 A1 * | 2/2015 | | G01N 33/6896 |
| WO | WO-2018148788 A1 * | 8/2018 | | C12Q 1/6883 |
| WO | WO-2021005568 A1 * | 1/2021 | | G01N 33/6896 |

OTHER PUBLICATIONS

Green, Auditory P50: A Potential Biomarker of Early Alzheimer's Disease and Relationship to Cerebrospinal Fluid Beta-Amyloid and Tau, Jun. 2014, Thesis for Drexel University (Year: 2014).*

Mielke et al., CSF sphingolipids, β-amyloid, and tau in adults at risk for Alzheimer's disease, Nov. 2014, Neurobiological Aging, vol. 35(11) (Year: 2014).*

Insel et al., Assessing risk for preclinical β-amyloid pathology with APIE, cognitive, and demographic information, 2016, Alzheimer's & Dementia: Diagnosis, Assessment & Disease Monitoring 4 (Year: 2016).*

Goudey et al., A blood-based signature of cerebral spinal fluid Aβ1-42 status, Sep. 2017, bioRxiv preprint (Year: 2017).*

Voyle et al., Genetic Risk as a Marker of Amyloid-β and Tau Burden in Cerebrospinal Fluid, 2017, Journal of Alzheimer's Disease, vol. 55 (Year: 2017).*

Miebach et al., Which features of subjective cognitive decline are related to amyloid pathology? Findings from the DELCODE study, Jul. 2019, Alzheimer's Research & Therapy (Year: 2019).*

Young et al., A data-driven model of biomarker changes in sporadic Alzheimer's disease, 2014, Brain 137 (Year: 2014).*

Huynh et al., Alzheimer's Disease: Biomarkers in the Genome, Blood, and Cerebrospinal Fluid, Mar. 20, 2017, Frontiers in Neurology (Year: 2017).*

Bilgel et al., Predicting time to dementia using a quantitative template of disease progression, Nov. 1, 2018, biorxiv (Year: 2018).*

Ho et al., Cognitive Profiling Relating to Cerebral Amyloid Beta Burden Using Machine Learning Approaches, Apr. 2019, Frontiers in Aging Neuroscience (Year: 2019).*

B. Goudey et al. "A blood-based signature of cerebrospinal fluid Aβ 1-42 status," Scientific Reports, vol. 9, article No. 4163, 2019.

S. Burnham et al., "A blood-based predictor for neocortical Aβ burden in Alzheimer's disease: results from the AIBL study." Molecular Psychiatry, 19, 519-526, 2014.

N. Ashton et al., "A plasma protein classifier for predicting amyloid burden for preclinical Alzheimer's disease." Science Advances, Feb. 6, 2019: vol. 5, No. 2, eaau7220 DOI: 10.1126/sciadv.aau7220.

S. Westwood, et al. "Plasma Protein Biomarkers for the Prediction of CSF Amyloid and Tau and [18F]-Flutemetamol PET Scan Result." Frontiers in Aging Neuroscience, vol. 10, article 409. Dec. 11, 2018, doi:10.3389 /fnagi.2018.00409.

Alzforum, "With Sudden Progress, Blood Aβ Rivals PET at Detecting Amyloid." Aug. 24, 2018 [Accessed Apr. 16, 2019] <https://www.alzforum.org/news/conference-coverage/sudden-progress-blood-av-rivals-pet-detecting-amyloid>.

B. Goudey et al., "Using Machine Learning to Improve Alzheimer's Screening," 14th International Conference on ALzheimer's & Parkinson's Disease in Lisbon, Portugal (Mar. 26-31, 2019), 45 pages.

B. Goudey et al., "A Machine Learning Approach to Predict CSF tau-181 from blood," 14th International Conference an Alzheimer's & Parkinson's Disease in Lisbon, Portugal (Mar. 26-31, 2019), 17 pages.

Swan et al., "Combining Genetic Risk Scores and Plasma Proteins For A Minimally Invasive Test for for pTau181/Aβ1-42 ratio," 14th International Conference on Alzheimer's & Parkinson's Disease in Lisbon, Portugal (Mar. 26-31, 2019), 11 pages.

Yang, Che-Chuan et al. 'Assay of Plasma Phosphorylated Tau Protein (Threonine 181) and Total Tau Protein in Early-Stage Alzheimer's Disease'. Jan. 1, 2018 : 1323-1332. [Abstract Only].

* cited by examiner

MACHINE LEARNING FOR AMYLOID AND TAU PATHOLOGY PREDICTION

BACKGROUND

Embodiments presented herein relate to using machine learning techniques to predict concentration levels of biological disease markers, and more specifically, to predict concentration levels of Alzheimer's disease biomarkers in cerebrospinal fluid based on patient demographics and protein/metabolite concentration levels in the blood.

Alzheimer's disease (AD) is a terminal neurodegenerative disease that has historically been diagnosed based on clinically-perceptible cognitive decline of an individual and the exclusion of other potential conditions. Recently, AD has been increasingly recognized as a gradual neurodegenerative process with biological risk factors in the brain being identifiable decades before cognitive changes become apparent. Thus, there is a strong demand for diagnostic methods of detecting AD risk factors prior to the onset of clinical dementia so that therapeutic intervention or care planning may be commenced sooner in AD progression.

There are two established cerebrospinal fluid (CSF) biomarkers for Alzheimer's disease: amyloid beta (Aβ) peptides and phosphorylated tau (p-tau). Aβ peptides are proteolytic fragments of the transmembrane amyloid precursor protein, whereas tau is a brain-specific, axon-enriched microtubule-associate protein. Currently, methods for measuring Aβ and p-tau levels include diagnostic analysis of extracted CSF fluid or Positron Emission Tomography (PET) of the brain. However, CSF collection is highly invasive and expensive and the accuracy of PET scans is suboptimal, as changes in Aβ PET pathology occur later in AD progression than in CSF Aβ pathology. A blood-based analysis, on the other hand, in combination with other easily-accessible measurements, would be a simpler route for AD screening, and would offer a tractable option for early screening of patients at risk.

Accordingly, what is needed in the art are improved methods of measuring Aβ and p-tau levels for AD pathogenesis based on a blood analysis and other non-invasive measurables.

SUMMARY

One embodiment of the present disclosure provides a method for predicting values of Aβ and p-tau concentration levels in CSF of a first patient. The method generally includes receiving a plurality of values relating to a plurality of attributes of a first patient. The plurality of values is provided to a machine learning model trained using data associated with a cohort of patients and configured to determine an association between the plurality of attributes and measured Amyloid-β (Aβ) and phosphorylated tau (p-tau) concentration levels in cerebrospinal fluid (CSF) of the cohort of patients. A predicted value for Aβ and p-tau concentration levels in CSF of the first patient is predicted based on the plurality of values and the machine learning model.

Another embodiment of the present disclosure provides a system having a processor and a memory. The memory generally has instructions stored thereon which, when executed by the processor, performs an operation for predicting values of Aβ and p-tau concentration levels in CSF of a first patient. The operation generally includes receiving a plurality of values relating to a plurality of attributes of a first patient. The plurality of values is provided to a machine learning model trained using data associated with a cohort of patients and configured to determine an association between the plurality of attributes and measured Amyloid-β (Aβ) and phosphorylated tau (p-tau) concentration levels in cerebrospinal fluid (CSF) of the cohort of patients. A predicted value for Aβ and p-tau concentration levels in CSF of the first patient is predicted based on the plurality of values and the machine learning model.

Still another embodiment of the present disclosure provides a computer-readable storage medium having computer-readable program code embodied therewith, the computer-readable program code executable by one or more computer processors to perform an operation. The operation generally includes receiving a plurality of values relating to a plurality of attributes of a first patient. The plurality of values is provided to a machine learning model trained using data associated with a cohort of patients and configured to determine an association between the plurality of attributes and measured Amyloid-β (Aβ) and phosphorylated tau (p-tau) concentration levels in cerebrospinal fluid (CSF) of the cohort of patients. A predicted value for Aβ and p-tau concentration levels in CSF of the first patient is predicted based on the plurality of values and the machine learning model.

DETAILED DESCRIPTION

Method and apparatus for predicting amyloid beta (Aβ) and phosphorylated tau (p-tau) biomarker levels in the cerebrospinal fluid (CSF) of patients. In an embodiment, values for a number of relatively-easy-to-measure attributes (e.g., measured or determined by non-invasive means), are used by a machine learning model to predict values for Aβ and/or p-tau biomarker levels for a given patient, without requiring invasive testing of CSF or PET scans. These predicted values can then be used to generate a probability that the patient will develop AD at a future time, generate a probability of a patient's predicted rate of AD progression, and/or generate a probability of a patient's age at the onset of dementia.

In an embodiment, data associated with a cohort of patients having known measurements of Aβ and p-tau biomarker levels, including determined values for the easily-measureable attributes, can be used to train a machine learning model. That trained model can then be provided with measured attributes for a given patient, and can use the measured attributes to predict Aβ and/or p-tau biomarker levels for the patient. These predicted values for Aβ and/or p-tau biomarker levels can then be used to generate a probability that the first patient will develop AD at a future time, generate a probability of a patient's predicted rate of AD progression, and/or generate a probability of a patient's age at the onset of dementia.

Figure 1:
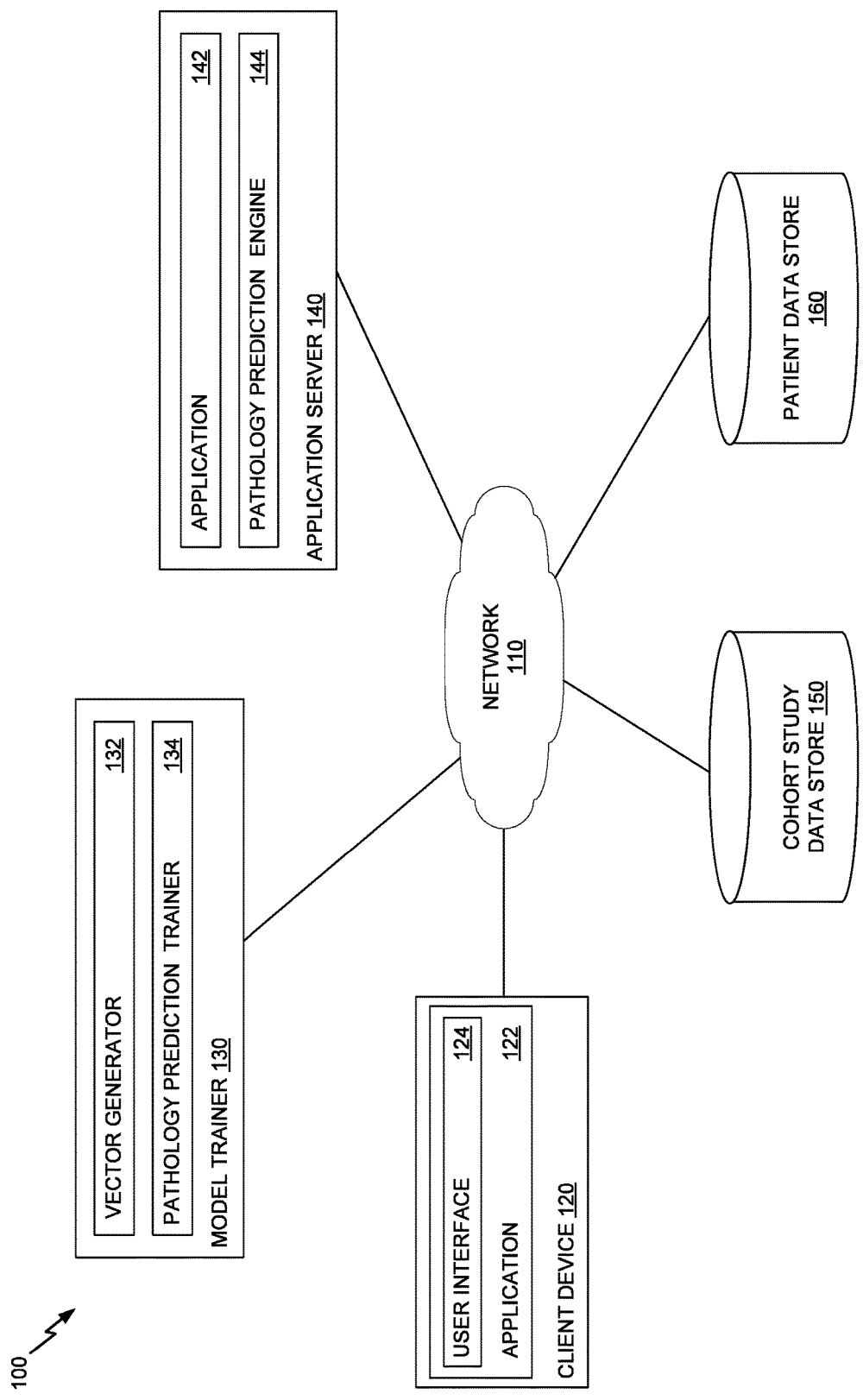
FIG. 1 illustrates an example network environment in which predictive cognitive models are used to predict a patient's AD biomarker pathology, for example, Aβ and p-tau pathology status, based on other patient attributes, according to one embodiment.

FIG. 1 illustrates an example network environment in which predictive cognitive models are used to predict a patient's AD biomarker pathology, for example, Aβ and p-tau pathology status, based on other patient attributes, according to one embodiment. As illustrated, computing environment 100 includes a client device 120, a model trainer 130, an application server 140, a cohort study data store 150, and a patient data store 160, connected via network 110.

Client device 120 generally is representative of a computing device on which a user can define and/or manage the training and use of machine learning models used by pathology prediction engine 144 to predict a patient's Aβ and p-tau pathology status and access application 142 on application server 140 to obtain a set of cohort study data for Aβ and p-tau pathology prediction. Client device 120 may be, for example, a laptop computer, a desktop computer, a thin client, a tablet computer, a mobile computing device, and the like. As illustrated, client device 120 includes a user interface 124. User interface 124 allows a user of a client device 120 to define a training data set for use in training machine learning models for predicting patient Aβ and p-tau pathology status.

Client device 120 includes an application 122 (e.g., a client side component of a client-server application) comprising a user interface 124, which allows a user of client device 120 to interact with a server side component, such as application 142 on application server 140. User interface 124 may, for instance, allow a user of client device 120 to initiate prediction of a patient's Aβ and p-tau pathology status by providing, to application server 140, medical information of the patient (e.g., in the form of patient attribute values).

Model trainer 130 generally uses medical information about patients previously enrolled in longitudinal AD cohort studies (e.g., from cohort study data store 150, which may include data from the Alzheimer's Disease Neuroimaging Initiative (ADNI) (http://adni.loni.usc.edu/)) to train predictive models used in predicting values of patient Aβ and p-tau pathology status, and in turn, future patient AD pathology status, based on easily-measureable (e.g., measured or determined by non-invasive means) patient attribute values. As illustrated, model trainer 130 includes a vector generator 132 and a pathology prediction trainer 134. The training data may include a first set of labeled data used to train the predictive models and a second set of unlabeled data (e.g., for which the intended label is known) used to verify the accuracy of the trained predictive models and to refine the trained predictive models prior to deployment to application server 140.

Vector generator 132 is generally configured to generate a training data set for use by pathology prediction trainer 134 to train a machine learning model for predicting a future patient's Aβ and p-tau pathology status based on their demographic characteristics, genetic characteristics, and/or blood-based signature (e.g., in the form of easily-measurable patient attributes, such as blood analyte concentration levels). To generate the training data set, vector generator 132 can obtain corresponding medical information about patients previously enrolled in AD cohort studies from cohort study data store 150. The information from cohort study data store 150 may include, for example, a roster of patients enrolled in the cohort study, easily-measurable patient attribute values, CSF-based patient attribute values, and patient clinical diagnoses (e.g., cognitively normal (CN), mild cognitive impairment (MCI), or having Alzheimer's disease (AD)).

In certain embodiments, a training data set for a particular predictive model may include, for example, a plurality of training data instances that include individual blood-based biomarker levels or combinations of blood-based biomarker levels. For example, blood-based biomarkers that may be included as features in training data instances include plasma-based proteins, such as amyloid-beta(aβ) 1-42, adiponectin, apolipoprotein, apolipoprotein A-IV, apolipoprotein C-I, apolipoprotein E (APOE), B lymphocyte chemoattractant, brain natriuretic peptide, c-reactive protein, chromogranin-A, ciliary neurotrophic factor, cortisol, creatine kinase-MB, eotaxin 3, interleukin-3, leptin, myeloid progenitor inhibitory factor 1, pancreatic polypeptide, placenta growth factor, receptor for advance glycosylation end products, serotransferrin, thyroxine-binding globulin, and vitronectin. In some examples, up to about 50 different plasma-based proteins may be included as features in training data instances. In other examples, about 50 or more different plasma-based proteins may be included as features in training data instances, such as about 150 or more different blood-based biomarkers and/or metabolites.

In certain embodiments, a training data set for a particular predictive model may additionally or alternatively include individual blood-based metabolites and/or lipids or combinations of metabolites and/or lipids. For example, blood-based metabolites and/or lipids that may be included as features in training data instances include sphingolipids such as hydroxysphingomyelin (SM ((OH)) C16:1 and SM (OH) C14:1, glycerophospholipids such as phosphatidylcholine acyl-alkyl (PC ae) C44:5 and PC ae C44:3, nitrotyrosine, creatinine, and the like.

Generally, the concentration levels of biomarkers and/or analytes described above may be measured from patient blood samples via any suitable methods, including but not limited to sandwich enzyme-linked immunosorbent assays (ELISA), Luminex assays, SOMAmer-based assays, Meso Scale assays, mass-spectrometry (MS)-based assays such as matrix-assisted laser desorption/ionization-time of flight MS (MALDI-TOF-MS), and the like.

In certain embodiments, a training data set for a particular predictive model may additionally or alternatively include features such as genetic characteristics. For example, a genetic characteristic that may be included as a feature in training data instances is the presence or absence of the Epsilon-4 (ε4) mutation in the patient's apolipoprotein E (APOE) gene. In another example, a genetic characteristic that may be included as a feature in training data instances includes a patient's polygenic hazard score (PHS) or genomic risk score (GRS) based on the presence or absence of a plurality of single nucleotide polymorphisms (SNPs) for predicting AD. In some examples, the plurality of SNPs may include millions of SNPs. In another example, expression of individual genes or a combination of genes may be included as a feature in training data instances.

In certain embodiments, a training data set for a particular predictive model may additionally or alternatively include features such as demographic characteristics. For example, a demographic characteristic that may be included as a feature in training data instances is a patient's age.

Accordingly, the training data may allow for the predictive model to be trained to predict values of patient Aβ and p-tau attributes based on cohort associates and/or trends. The values of patient Aβ and p-tau attributes may be binary variables indicating whether the Aβ or p-tau attribute is normal or abnormal. In some embodiments, the values of patient Aβ and p-tau attributes may be numerical values. In further embodiments, the predictive model is trained to output a confidence score along with each predicted value of patient Aβ and p-tau attributes. These confidence scores may be used in determining a risk (e.g., probability) of future AD pathology, determining a predicted rate of AD progression, and/or determining a predicted age of onset.

To generate the training data to be used by pathology prediction trainer 134, vector generator 132 can generate a first set of training data comprising feature data and label data used to train a machine learning model and a second set of unlabeled feature data (e.g., provided as unlabeled data to the predictive model for validation purposes) that can be used to test the generated predictive model. For example, in an embodiment where machine learning techniques are used to predict values of Aβ and p-tau attributes of a patient, the first set of data may comprise a plurality of vectors, where the features in each vector include information from cohort study data store 150 (e.g., attributes of previously-enrolled patients including demographic characteristics, genetic characteristics, blood biomarker levels, and CSF biomarker levels) and the labels in each vector include a subsequent value of an attribute. The second set of data may comprise an unlabeled set of patient data associated with patients having a clinically (phenotypically) determined diagnosis and/or pathology status.

Pathology prediction trainer 134 obtains the training data generated by vector generator 132 and, using supervised or unsupervised learning techniques, trains one or more predictive models for predicting Aβ and p-tau attribute values, a risk of future AD pathology, a rate of AD progression, and/or an age of AD onset for a given patient. Training predictive models may involve using a training data set that includes training inputs that are associated with particular training outputs (e.g., labels). In some embodiments, the predictive model also outputs a confidence score with a predicted Aβ and p-tau attribute value. Pathology prediction trainer 134 may use different training data generated by vector generator 132 to train a predictive model to accept a set of patient Aβ and p-tau attribute values as inputs to output a risk value of future AD pathology, a predicted rate of AD progression, and/or a predicted age of onset for the patient.

Predictive models described herein may be, for example, random forest models, and training a prediction model may involve building a "forest" of "trees" representing the training data, where input features are randomly permuted at each split (e.g., each division of the training data). In such embodiments, a prediction model is "trained" by constructing a plurality of decision trees based on sub-divisions of the training data that include random permutations of input features associate with labels. Random forest models may be effective at predicting Aβ and p-tau attribute values of patients, and determining the risk of future AD pathology for a given patient, while avoiding noise present in the measured inputs. It is noted that random forest techniques are only included as one example, and that other techniques may be employed for training prediction models. Other types of machine learning models, such as least absolute shrinkage and selection operator (LASSO) regression, logistic regression, decision tree, gradient-boosted tree, Naïve Bayes model, multilayer perceptron, and other may also be used as prediction models.

In certain embodiments a single prediction model is used, while in other embodiments a plurality (or ensemble) of prediction models may be used (e.g., for different sets of inputs and/or different stages of an overall process for predicting patient pathology). In some embodiments, additional patient attributes to those described above may be used to customize a generated prediction model and thus customize the results delivered by the pathology prediction engine 144. Techniques described herein may be used as part of a larger process for predicting patient Aβ and p-tau pathology and/or determining risk, progression, and/or onset of future AD pathology. For example, predicting a patient's Aβ and p-tau pathology may be an initial step that is performed before using additional predictive models to determine a risk of future AD pathology.

Application server 140 includes an application 142 and a pathology prediction engine 144. Application 142 may be any type of application in which users can request a prediction of a patient's Aβ and p-tau pathology status by providing patient data (e.g., medical information such as blood-based biomarker levels, genetic characteristics, and/or demographic characteristics). Client device 120 may instantiate or initiate a session of application 142 in response to a request for application content (e.g., prediction of Aβ and p-tau pathology status and a confidence score) generated by a user of client device 120. In some embodiments, the instance of a session of application 142 may be instantiated by a user of client device 120 accessing a home page of an application 142 structured as a web application. In other embodiments, user interface 124 may instantiate the instance of application 142 by launching an executable file on client device that includes components that execute locally on client device 120 and use data provided by the application 142.

During execution of application 142, a user of client device 120 may request a prediction of a patient's Aβ and p-tau pathology status (e.g., a patient's Aβ and p-tau attribute values) by providing data related to that patient to application 142 in conjunction with an analysis request. In response, application 142 provides the received data to pathology prediction engine 144 for analysis. In some embodiments, the user may provide identifying information for a patient (e.g., name, patient number, date of birth, social security number, and/or other identifying information), and data (e.g., medical information, such as easily-measurable patient attributes) for the patient may be retrieved (e.g., by pathology prediction engine 144) from patient data store 160 based on the identifying information. Application 142 may receive a prediction of the patient's Aβ and p-tau attribute values from pathology prediction engine 144, as discussed in further detail below, and display the prediction of the patient's Aβ and p-tau attribute values in user interface 122 of client device 120. In some embodiments, the prediction of the patient's Aβ and p-tau attribute values is displayed as binary variable. For example, the prediction of the patient's Aβ and/or p-tau attribute values may display as "normal" or "abnormal." In further examples, the prediction of the patient's Aβ and p-tau attribute values and may include a metric value. In still further examples, the prediction of the patient's Aβ and p-tau attribute values may include a confidence score for each prediction.

Pathology prediction engine 144 uses the prediction model(s) generated by pathology prediction trainer 134, as discussed above, to analyze patient data for a given patient and predict the patient's Aβ and p-tau attribute values based, at least in part, on the patient's easily-measurable attributes (e.g., blood-based biomarker levels, genetic characteristics, and/or demographic characteristics). In some embodiments, pathology prediction engine 144 retrieves patient data, such as medical information, for a given patient from patient data store 160 based on identifying information of the patient (e.g., received from a user of client device 120). Patient data may include a plurality of different types of patient attributes, such as the easily-measurable patient attributes discussed above. In some embodiments, pathology prediction engine 144 predicts future attributes of a given patient, such as by providing measured or predicted current attributes of the patient (e.g., predicted Aβ and p-tau attribute values or measured attributes retrieved from patient data store 160) as inputs to one or more predictive models that output predicted future attributes (e.g., future AD pathology status), which may be accompanied in some embodiments by confidence scores.

Pathology prediction engine 144 provides measured patient attributes (e.g., easily-measurable attributes such as blood-based biomarker levels, genetic characteristics, and/or demographic characteristics) of the given patient as inputs to one or more predictive models for predicting Aβ and p-tau attribute values (with scores) for the given patient. For example, a predictive model may process the inputs and output a value for each of the patient's predicted Aβ and p-tau attribute values, each value indicating predicted levels of Aβ or p-tau in the patient's CSF. Techniques described herein may involve fuzzy logic, as output values are not only based on binary variables (e.g., whether or not a patient is a carrier of the ε4 mutation), but are based on degrees of association (e.g., concentration levels of plasma-based proteins). Predictive models, therefore, are a means of implementing fuzzy logic.

Cohort study data store 150 may be a data storage entity, such as a database or repository, that stores medical information about patients previously enrolled in longitudinal AD cohort studies. For example, cohort study data store 150 may store rosters of patients that participated in AD cohort studies, patient attribute values, and patient clinical diagnoses. The patient attribute values may include demographic characteristics, genetic characteristics, blood-based biomarker levels (e.g. plasma-based proteins, metabolites, and lipids), CSF-based biomarker levels, and/or the like. For example, the data in cohort study data store 150 may have been entered by one or more users (e.g., clinicians or professionals), or may have been mined from various sources, such as articles and reports related to cohort studies.

Patient data store 160 may be a data storage entity, such as a database or repository, that stores data about patients. For example, patient data store 160 may store personal data, easily-measureable patient attribute values, and other data related to patients, which may have been provided by one or more users, such as patients and/or clinicians and professionals.

While model trainer 130, application server 140, cohort study data store 150, and patient data store 160 are illustrated as separate components in FIG. 1, it should be noted that model trainer 130, application server 140, cohort study data store 150, and patient data store 160 may be implemented on any number of computing systems, either as one or more standalone systems or in a distributed environment.

Figure 2:
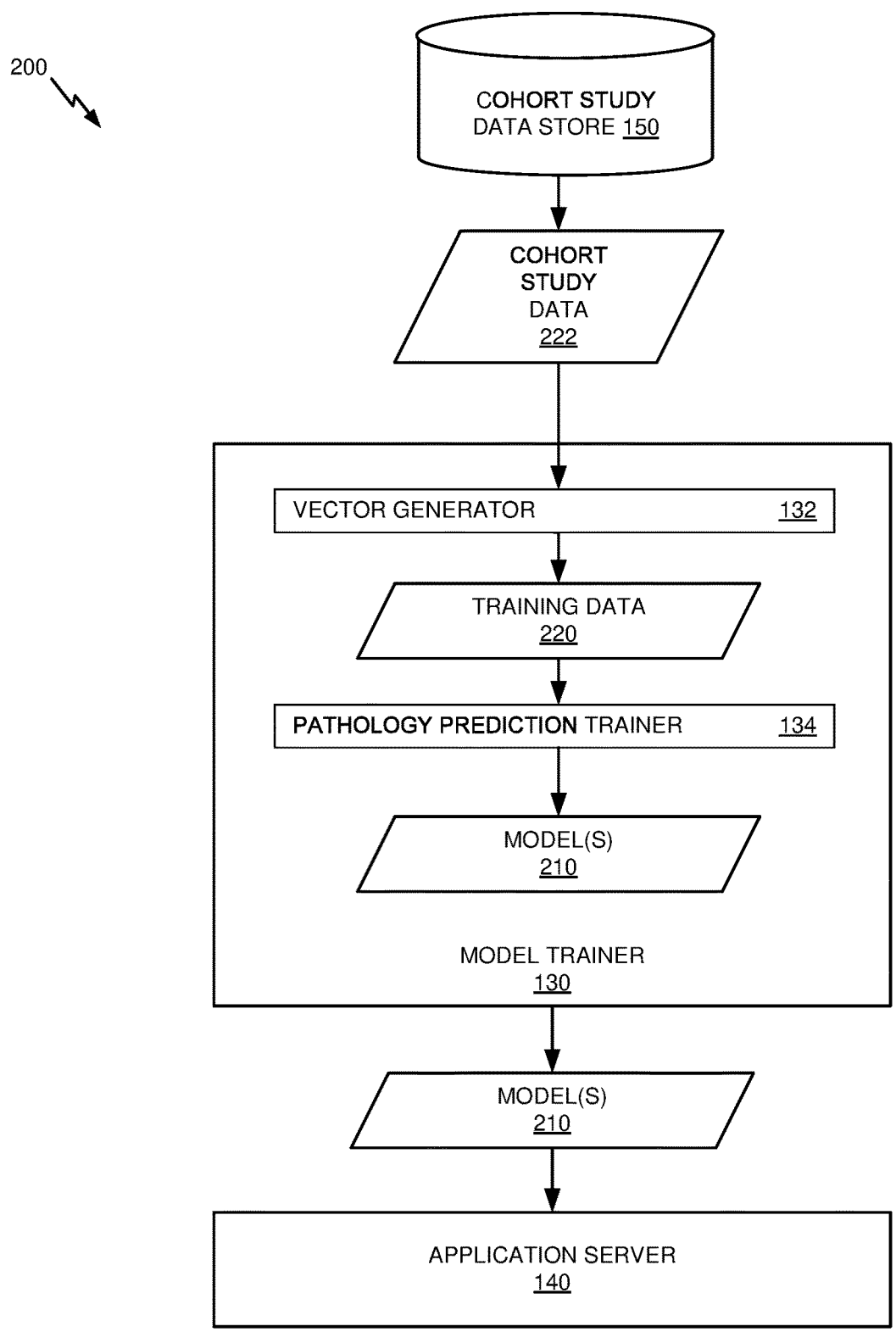
FIG. 2 illustrates example operations for training predictive models for predicting a patient's AD biomarker pathology based on other patient attributes, according to one embodiment.

FIG. 2 illustrates example operations for training predictive models for predicting a patient's AD biomarker pathology based on other patient attributes, according to one embodiment. Specifically, FIG. 2 illustrates an example 200 of training predictive models for predicting patient Aβ and p-tau attribute values as describe herein. Example 200 includes, in one embodiment, model trainer 130 (comprising vector generator 132 and pathology prediction trainer 134), cohort study data store 150, and application server 140 of FIG. 1.

Model trainer 130 retrieves cohort study data 222 from cohort study data store 150. Cohort study data store 150 may include medical information about patients previously enrolled in longitudinal AD cohort studies, such as demographic characteristics, genetic characteristics, blood biomarker levels, CSF biomarker levels, and/or clinical diagnosis.

Vector generator 132 uses cohort study data 222 to generate training data 220 for generating one or more trained models 210. For example, training data 220 may include a first training data set, each training data instance of the set associating attribute values of a plurality of patient attributes with an Aβ and/or p-tau attribute value. Another training data set in training data 220 may include associations between a plurality of patient attributes and clinical diagnoses of the patients.

Training data 220 is provided to pathology prediction trainer 134, which uses training data 220 to generate one or more trained models 210, such as using various unsupervised machine learning concepts. One or more models 210 may be trained to output predicted Aβ and/or p-tau attribute values for a given patient, in some cases with confidence scores, based on other measured attribute values of the patient (e.g., by identifying associations and/or trends in patients having similar attribute values for the cohort studies, which may be accomplished using training data). Other models may be trained to output a predicted risk of future AD pathology, a predicted rate of AD progression, and/or a predicted age of AD onset for a given patient based on current and/or predicted attribute values.

Model trainer 130 provides the one or more models 210 to application server 140, which loads the one or more models into memory for use in predicting Aβ and p-tau attribute values, risk of future AD pathology, rate of AD progression, and/or age of onset for patients.

Figure 3:
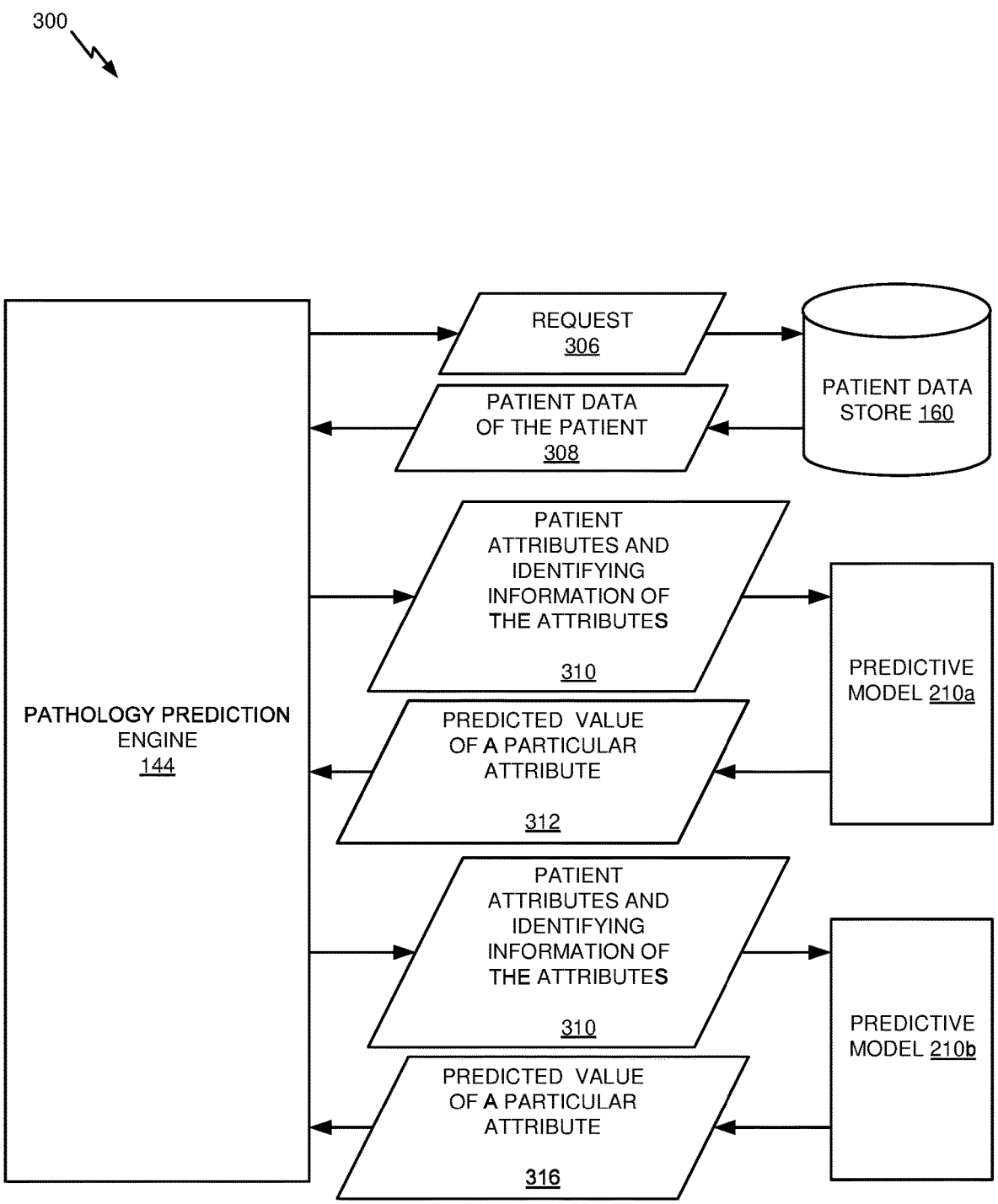
FIG. 3 illustrates example operations for using trained predictive models to predict a patient's AD biomarker pathology based on other patient attributes, according to one embodiment.

FIG. 3 illustrates example operations for using trained predictive models to predict a patient's AD biomarker pathology based on other patient attributes, according to one embodiment. Specifically, FIG. 3 illustrates an example 300 of using trained predictive models to predict Aβ and p-tau attribute values for patients. Example 300 includes, in an embodiment, pathology prediction engine 144, patient data store 160, and cohort study data store 150 of FIG. 1. Example 300 also includes predictive model 210a and 210b, which may be models 210, trained as illustrated in example 200 of FIG. 2. In example 300, predictive model 210a is trained to predict an Aβ attribute value of a given patient based on easily-measurable patient attributes (e.g., demographic characteristics, genetic characteristics, and/or blood biomarker levels) that may provide information about the Aβ attribute value. Predictive model 210b is trained to predict a p-tau attribute value of a given patient based on easily-measurable patient attributes (e.g., demographic characteristics, genetic characteristics, and/or blood biomarker levels) that may provide information about the p-tau attribute value.

Pathology prediction engine 144 sends a request 306 to patient data store 160 for patient data related to a given patient, such as in response to a request from a user of a client device for a prediction of the patient's Aβ and/or p-tau attribute values. Patient data store 160 provides patient data 308 of the patient to pathology prediction engine 144 in response to request 306. Patient data 308 may, for instance, include patient attributes such as the easily measurable patient attributes described above (e.g., demographic characteristics, genetic characteristics, and/or blood biomarker levels). Additionally, patient data 308 may further include other historical and/or diagnostic medical information relevant in predicting Aβ and/or p-tau attribute values.

Pathology prediction engine 144 provides current patient attributes (e.g., from patient data 308) and identifying information of the current patient attributes 310 as inputs to predictive model 210*a*, which outputs one or more predicted values of the particular attribute 312 (e.g., Aβ levels in CSF), which may include one or more predicted values of the particular attribute 312 at one or more future points (e.g., at particular intervals).

Additionally or alternatively, pathology prediction engine 144 provides current patient attributes (e.g., from patient data 308) and identifying information of the current patient attributes 310 as inputs to predictive model 210*b*, which outputs one or more predicted values of the particular attribute 316 (e.g., p-tau levels in CSF), which may include one or more predicted values of the particular attribute 316 at one or more future points. In some examples, the values of the particular attribute 316 are predicted simultaneously with the values of the particular attribute 312.

In some examples, pathology prediction engine 144 may predict whether the patient has normal or abnormal levels of Aβ and/or p-tau in the patient's CSF based on the outputs by predictive models 210*a* and/or 210*b*. For instance, if the predictions are above a threshold, pathology prediction engine 144 may determine that the patient has abnormal levels of Aβ and/or p-tau. In another example, pathology prediction engine 144 may predict a value range of Aβ and/or p-tau in the patients CSF based on the outputs by predictive models 210*a* and/or 210*b*. For instance, pathology prediction engine 144 may predict a value range of Aβ and/or p-tau and a clinician or professional may make a determination of Aβ and/or p-tau pathology status (e.g., normal or abnormal) based on the predicted value range.

Figure 4:
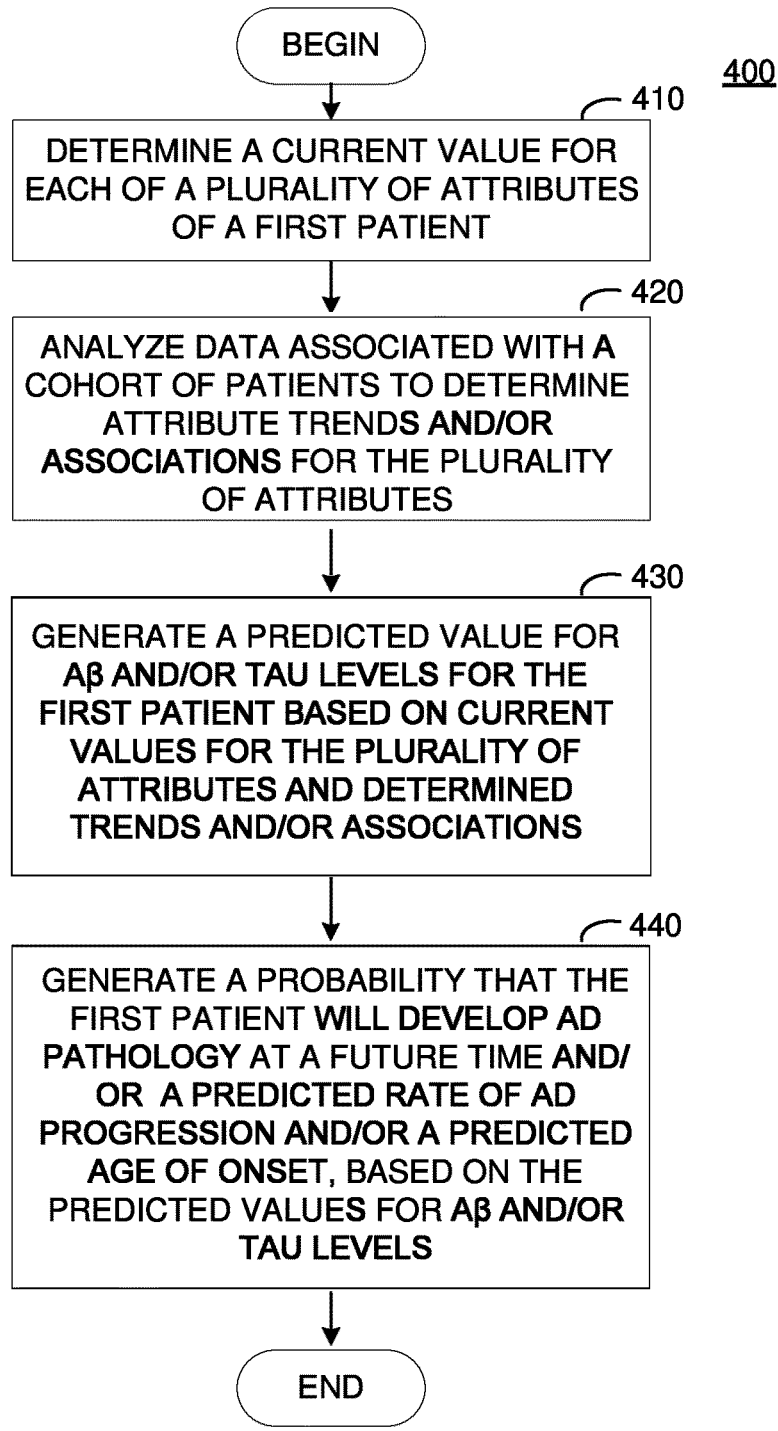
FIG. 4 illustrates example operations for delivering a patient's AD biomarker pathology prediction based on the application of a predictive model to the determined values patient's easily-measureable attributes.

FIG. 4 illustrates example operations for delivering a patient's AD pathology prediction based on the application of a predictive model to the determined values for a patient's easily-measureable attributes. Specifically, FIG. 4 illustrates an example 400 for predicting Aβ and p-tau levels in the CSF, risk of future AD pathology, rate of AD progression, and/or age of onset for a given patient. For example, operations 400 may be performed by pathology prediction engine 144 of FIGS. 1 and 3.

At step 410, a current value for each of a plurality of attributes of a first patient is determined. For example, pathology prediction engine 144 of FIG. 1 may determine the current values for the plurality of attributes based on data retrieved from patient data store 160 of FIG. 1.

At step 420, data associated with a cohort of patients is analyzed to determine attribute associates and/or trends for the plurality of easily-measured attributes in relation to measured CSF Aβ and p-tau levels. For example, pathology prediction engine 144 of FIG. 1 may provide values for the plurality of easily-measured attributes of the first patient as inputs to a predictive model, and the predictive model may determine attribute associations and/or trends for the plurality of easily-measured attributes according to its training based on attribute values in relation to measured CSF Aβ and p-tau levels of cohort patients.

At step 430, predicted attribute values for Aβ and/or p-tau levels for the first patient are generated based on the values of the first patient's easily-measureable attributes. For example, the predictive model may output the predicted attribute values for Aβ and/or p-tau levels for the first patient by applying the attribute associations and/or trends to the current values for each of the plurality of easily-measurable attributes of the first patient. In one example, the attribute associations and/or trends comprise one or more correlations between concentration levels of blood-based proteins and concentrations levels of CSF-based Aβ and/or p-tau, and the predicted attribute values for Aβ and/or p-tau levels of the first patient may be generated based on the one or more correlations between concentration levels of blood-based proteins and concentrations levels of CSF-based Aβ and/or p-tau.

Additionally or alternatively, the predicted attribute values for Aβ and/or p-tau levels of the first patient may be generated based on correlations between demographic characteristics and/or genetic characteristics and concentrations levels of CSF-based Aβ and/or tau. Additionally, or alternatively, the predicted attribute values for Aβ and/or tau levels of the first patient may be generated based on correlations between concentration levels of blood-based metabolites or lipids and concentrations levels of CSF-based Aβ and/or tau.

The predicted attribute values for Aβ and/or p-tau levels for the first patient may be used to determine a risk (e.g., probability) that the first patient will develop AD at a future time, a predicted rate of AD progression, and/or a predicted age of AD onset. Thus, at step 440, the risk that the first patient will develop AD pathology at a future time is generated based on the predicted attribute values for Aβ and/or p-tau levels. In one example, the predicted attribute values for Aβ and/or p-tau levels may be provided as inputs to a predictive model, which may output the risk value. Additionally or alternatively, a predicted rate of AD progression and/or a predicted age of AD onset for the first patient may be generated based on the predicted attribute values for Aβ and/or p-tau levels at step 440.

It is noted that while embodiments are described as involving predictive models using machine learning techniques, certain aspects of the present disclosure may be performed without the use of predictive models. For example, the risk of the first patient developing AD at a future time may be determined based on confidence scores associated with predicted attribute values of Aβ and/or p-tau levels output by a predictive model rather than by providing the predicted attribute values to a separate predictive model to determine the risk. In another example, the risk of the first patient developing AD at a future time may be determined by a clinician or professional based on the predicted attribute values of Aβ and/or p-tau levels output by a predictive model.

Figure 5:
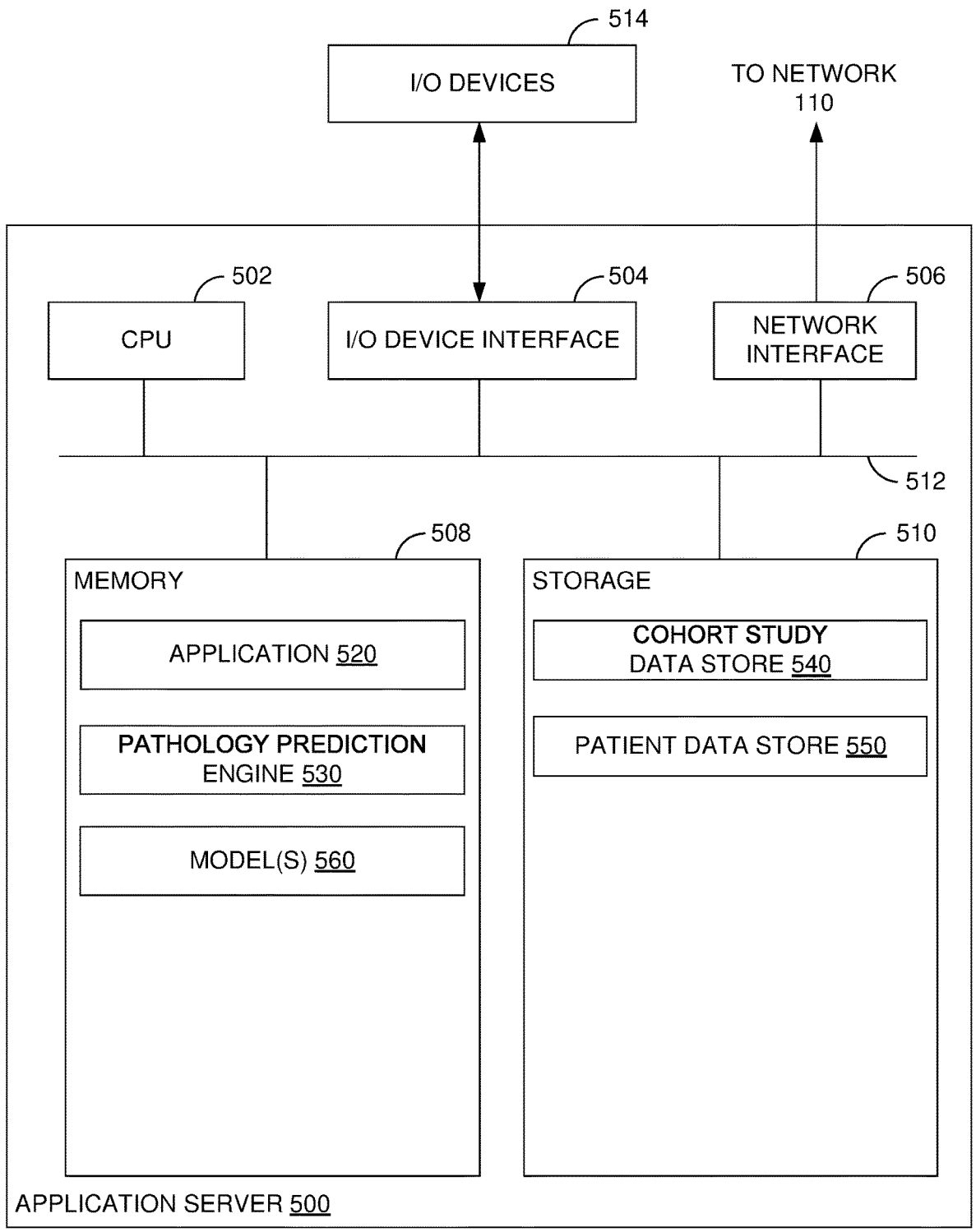
FIG. 5 illustrates an example system in which aspects of the present disclosure may be performed.

FIG. 5 depicts a computing system 500 with which embodiments of the present disclosure may be implemented. For example, computing system 00 may represent application server 140 of FIG. 1.

System 500 includes a central processing unit (CPU) 502, one or more I/O device interfaces 504 (that may provide connections for various I/O devices 514, such as keyboards, displays, mouse devices, and the like) to the system 500, network interface 506 (e.g., a physical network interface card), memory 508, storage 510, and an interconnect 512. It is noted that one or more components of system 500 may alternatively be located remotely and accessed via a network, such as network 110. It is further contemplated that one or more components of system 500 may comprise physical or virtualized components.

CPU 502 may receive and execute instructions stored in memory 508. Similarly, the CPU 502 may receive and store data related to application in memory 508. The interconnect 512 transmits programming instructions and application data, among the CPU 502, I/O device interface 504, network interface 506, memory 508, and storage 510. CPU 502 is included to be representative of a single CPU, multiple CPUs, a single CPU having multiple processing cores, and other arrangements.

Additionally, the memory 508 may represent a random access memory. Storage 510 may be a disk drive, a solid state drive, or a collection of storage devices distributed across multiple storage systems. Although shown as a single unit, the storage 510 may be a combination of fixed and/or removable storage devices, such as fixed disc drives, removable memory cars or optical storage, network attached storage (NAS), or a storage area-network (SAN).

Storage 510 comprises clinical trial data store 540 and patient data store 550, which are representative of cohort study data store 150 and patient data store 160 of FIG. 1. As shown, memory 508 includes application 520, pathology prediction engine 530, and model(s) 560, which are representative of application 142 and pathology prediction engine 144 of FIG. 1 and model(s) 210 of FIG. 2.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., application 142 and/or pathology prediction engine 144 of FIG. 1) or related data available in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A computer-implemented method comprising:
receiving, on a computing system, a plurality of values relating to a plurality of attributes of a first patient, the plurality of attributes comprising at least blood-based biomarker levels of the first patient;
training, on the computing system, a machine learning model using data associated with a cohort of patients to determine an association between the plurality of attributes and measured Amyloid-$\beta$ (A$\beta$) and phosphorylated tau (p-tau) concentration levels in cerebrospinal fluid (CSF) of the cohort of patients, the data comprising at least blood-based biomarker levels and corresponding clinical diagnoses of the cohort of patients;
providing, by the computing system, the plurality of values to the trained machine learning model;
generating, by the computing system, a predicted value for A$\beta$ and p-tau concentration levels in CSF of the first patient, based on the plurality of values and using the trained machine learning model; and
based on the predicted value, generating, by the computing system, a probability that the first patient will develop Alzheimer's disease pathology and a predicted age of Alzheimer's disease pathology onset.

2. The method of claim 1, further comprising:
generating, by the computing system, a predicted rate of Alzheimer's disease pathology progression.

3. The method of claim 1, wherein the plurality of attributes comprises concentration levels of plasma-based proteins.

4. The method of claim 3, wherein the plasma-based proteins include A$\beta$1-42, apolipoprotein E, chromogranin-A, and eotaxin 3.

5. The method of claim 3, wherein the plurality of attributes further comprises genetic characteristics.

6. The method of claim 5, wherein the genetic characteristics include a binary variable indicating a presence of an epsilon-4 ($\epsilon$4) mutation in an apolipoprotein E gene.

7. The method of claim 3, wherein the plurality of attributes further comprises demographic characteristics.

8. The method of claim 1, wherein the predicted value for A$\beta$ and p-tau concentration levels in CSF of the first patient is generated without testing CSF for the first patient.

9. The method of claim 1, wherein the trained machine learning model comprises a random forest model.

10. A system, comprising:
a processor; and
a memory having instructions stored thereon which, when executed by the processor, perform an operation, the operation comprising:
receiving a plurality of values relating to a plurality of attributes of a first patient, the plurality of attributes comprising at least blood-based biomarker levels of the first patient;
training a machine learning model using data associated with a cohort of patients to determine an association between the plurality of attributes and measured Amyloid-β(Aβ) and phosphorylated tau (p-tau) concentration levels in cerebrospinal fluid (CSF) of the cohort of patients, the data comprising at least blood-based biomarker levels and corresponding clinical diagnoses of the cohort of patients;
providing the plurality of values to the trained machine learning model; and
generating a predicted value for Aβ and p-tau concentration levels in CSF of the first patient, based on the plurality of values and using the trained machine learning model; and
based on the predicted value, generating a probability that the first patient will develop Alzheimer's disease pathology and a predicted age of Alzheimer's disease pathology onset.

11. The system of claim 10, further comprising:
generating a predicted rate of Alzheimer's disease pathology progression.

12. The system of claim 10, wherein the plurality of attributes comprises concentration levels of plasma-based proteins.

13. The system of claim 12, wherein the plasma-based proteins include Aβ-42, apolipoprotein E, chromogranin-A, and eotaxin 3.

14. The system of claim 12, wherein the plurality of attributes further comprises genetic characteristics.

15. The system of claim 14, wherein the genetic characteristics include a binary variable indicating a presence of an epsilon-4 (ε4) mutation in an apolipoprotein E gene.

16. The system of claim 12, wherein the plurality of attributes further comprises demographic characteristics.

17. The system of claim 10, wherein the predicted value for Aβ and p-tau concentration levels in CSF of the first patient is generated without testing CSF for the first patient.

18. The system of claim 10, wherein the trained machine learning model comprises a random forest model.

19. A computer-implemented method comprising:
receiving, on a computing system, a plurality of values relating to a plurality of attributes of a first patient, the plurality of attributes comprising at least blood-based biomarker levels, metabolite levels, and a genomic risk score of the first patient, the genomic risk score based on the presence or absence of a plurality of single nucleotide polymorphisms;
training, on the computing system, a machine learning model using data associated with a cohort of patients to determine an association between the plurality of attributes and measured Amyloid-β (Aβ) and phosphorylated tau (p-tau) concentration levels in cerebrospinal fluid (CSF) of the cohort of patients, the data comprising blood-based biomarker levels, metabolite levels, a genomic risk score, and corresponding clinical diagnoses of the cohort of patients;
providing, by the computing system, the plurality of values to the trained machine learning model;
generating, by the computing system, a predicted value for Aβ and p-tau concentration levels in CSF of the first patient, based on the plurality of values and using the trained machine learning model; and
based on the predicted value, generating, by the computing system, a probability that the first patient will develop Alzheimer's disease pathology.

20. The method of claim 19, wherein the blood-based biomarker levels of the cohort of patients comprise plasma-based proteins, the plasma-based proteins comprising amyloid-beta(aβ) 1-42, adiponectin, apolipoprotein, chromogranin, creatine kinase-MB, eotaxin 3, interleukin-3, and leptin.

* * * * *